United States Patent

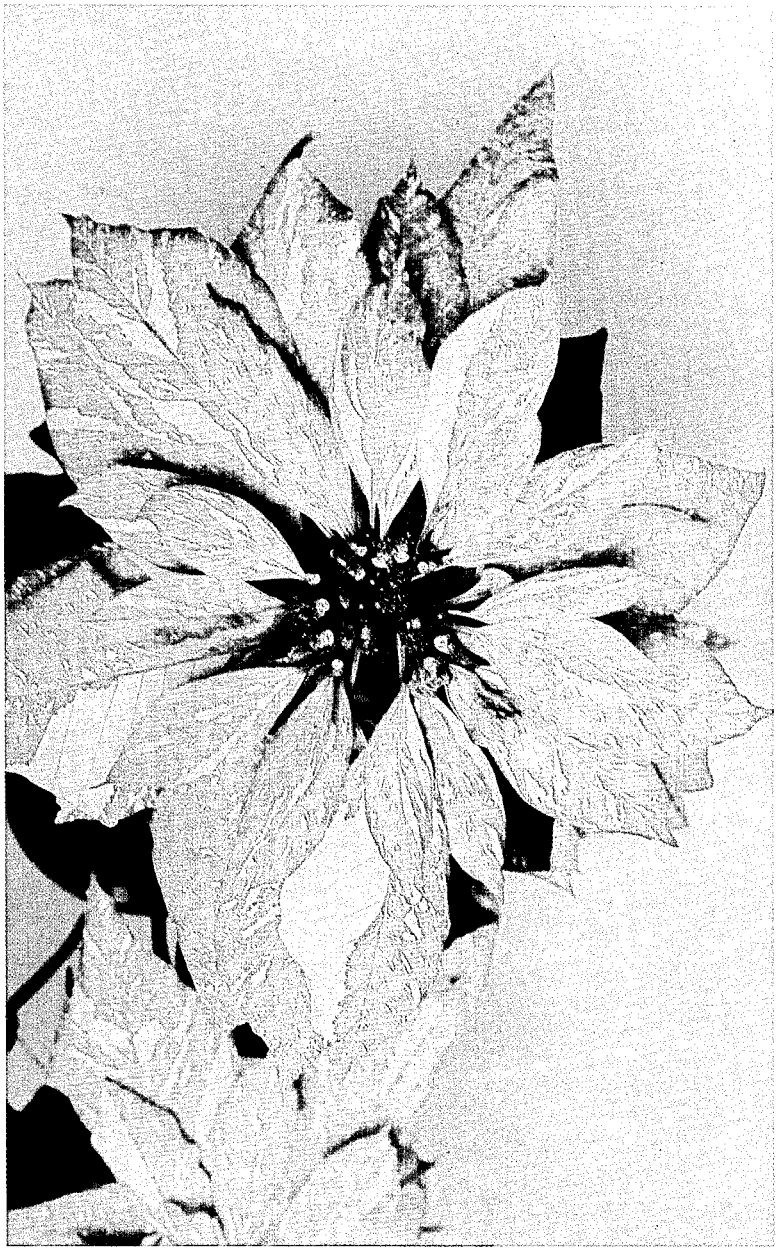

Plant Pat. 3,889

Patented May 18, 1976

3,889

POINSETTIA PLANT

John W. Fantom, Baltimore, Md., assignor to Fantom & Gahs Greenhouses, Inc., Baltimore, Md.

Filed Mar. 19, 1975, Ser. No. 559,815

Int. Cl. A01h *5/00*

U.S. Cl. Plt.—86 1 Claim

The present invention relates to a new and distinctive cultivar of poinsettia plant known by the varietal name Jingle Bells, and botanically known as *Euphorbia pulcherrima.*

The new cultivar is a sport of Eckespoint C–1 Red, a commercially available cultivar disclosed and claimed in U.S. Plant Pat. 2,923, granted on Sept. 30, 1969 to Paul Ecke.

The new cultivar was discovered as follows: About Dec. 12, 1971 at Fantom and Gahs Greenhouses, Inc., located in Baltimore County, Md., applicant found one branched Eckespoint C–1 Red which had three bracts, each of a different color. One bract was red, one was pink and one was variegated red and pink. The branch with the variegated bracts had eight leaves, and this branch was propagated by taking eight leaf bud cuttings which were revegetated and subsequently flowered in December 1972. Of these eight cuttings 4 or 5 flowered in 1972 with variegated bracts and the others flowered with pink bracts. Most branched plants in 1973 flowered with all variegated bracts (generally three branches per pinched plant) and some with combination variegated and pink bracts and a few all pink. By selection, the branched plants which produced all variegated bracts were saved and these plants retained the distinctive characteristics through successive propagation in 1974.

The new cultivar was initially asexually reproduced by cuttings in the greenhouses of Fantom & Gahs Greenhouses, Inc., Baltimore, Md., and was subsequently asexually reproduced at Ornamentals Laboratory, U.S. Department of Agriculture, Beltsville, Md., and Paul Ecke Poinsettias, Encinitas, Calif.

The new cultivar has been found to retain its distinctive characteristics through successive propagations.

The following characteristics distinguish the new cultivar from its parent and from other poinsettias commercially known and used in the floriculture industry:

1. The new cultivar is distinguished primarily by its variegated bract color, with the bracts being generally reddish in color and having pink blotches and spots.

2. Leaf shape—the margin is more entire and not as lobed in general as Eckespoint C–1 Red.

3. Petiole color—lighter red than Eckespoint C–1 red.

The accompanying colored photographic drawing is a top plan view of the bracts, with the colors being as true as possible to obtain in color reproductions of this type.

The following is a detailed description of the new cultivar based on plants produced under commercial practices in the greenhouses of Fantom and Gahs Greenhouses, Inc., 3611 E. Joppa Rd., Baltimore, Md. 21234. Color references are to the Munsell Color Limit Cascade, 1972 edition, except where general color terms of ordinary dictionary significance are used.

Parentage: The new cultivar is a sport of Eckespoint C–1. Red.

Form of plant: Medium tall and upright.

Growth habit: Vigorous branching when pinched.

Rooting: Soft wood cuttings easily root in a few weeks.

Blooming season: Under natural conditions in mid-December in 62° greenhouse under natural day length. By greenhouse culturing, the new cultivar can be forced into bloom in 9 weeks after start of long nights (14 hours) in summer, and 11 weeks in winter.

Foliage:

*Size.*—Normal.

*Quantity.*—Normal.

*Color.*—New foliage: Upper side—medium green, 20–14. Under side — lighter green, 22–13. Old foliage: Tends to tinge pink upon maturation.

*Shape.*—Generally ovate.

*Texture.*—Upper side — chartaceous to coriaceous. Under side—same.

*Edge or margin.*—Entire, lobed only occasionally.

*Apex.*—Acute.

*Disease resistance.*—Very good.

Flowers: (Cyathia).

*Borne.*—In cymes, surrounded by bracts.

*Quantity.*—About 20–25.

*Continuity.*—Development is in close succession.

*Buds.*—Complete — both stamens and pistil in same bud and they set fruit perhaps 25% of the time, which seems more abundant than the average for the parent cultivar and other commercial varieties observed.

*Bracts.*—Overall appearance of bracts is that they are large and fairly round, horizontal to slightly drooping. Individual bract form varies from elliptic to ovate; most are narrow but others are ⅔ as broad as long. Bracts are generally flat to slightly cupping from side to side. Texture is fairly smooth with very little puckering. Color: Top—Brick Red 40–10 with pale pink spots and blotches, 39–3. Under —Same. Generally—From a distance of about 10 feet or more, the general color appears to be red with white spots and blotches. On closer observation the base color is a brick red with pale pink spots and blotches.

*Reproductive organs.*—Stamens: Color, Red, 38–8. Pollen: Color, Yellow-gold 27–9. Styles: Color, Red at top near stigma turning to Light Green. Ovaries: Color, Green, 21–10.

I claim:

1. A new and distinct cultivar of poinsettia plant characterized particularly by its variegated bracts, which have a generally brick red base color and pink spots and blotches.

No references cited.

ROBERT E. BAGWILL, Primary Examiner